(12) United States Patent
Jin et al.

(10) Patent No.: US 9,700,282 B2
(45) Date of Patent: Jul. 11, 2017

(54) ULTRASOUND SYSTEM AND METHOD OF DETECTING PRESSURE APPLIED TO OBJECT

(71) Applicant: SAMSUNG MEDISON CO., LTD., Hongcheon-gun, Gangwon-Do (KR)

(72) Inventors: Gil-ju Jin, Gangwon-do (KR); Mi-ri Kim, Gangwon-do (KR); Saidmurod Akramov, Gangwon-do (KR); Mi-jeoung Ahn, Gangwon-do (KR); Dong-gyu Hyun, Gangwon-do (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 252 days.

(21) Appl. No.: 14/259,810

(22) Filed: Apr. 23, 2014

(65) Prior Publication Data
US 2014/0357994 A1 Dec. 4, 2014

(30) Foreign Application Priority Data
May 29, 2013 (KR) ........................ 10-2013-0061038

(51) Int. Cl.
*A61B 8/00* (2006.01)
*A61B 8/08* (2006.01)

(52) U.S. Cl.
CPC ............ *A61B 8/4444* (2013.01); *A61B 8/429* (2013.01); *A61B 8/485* (2013.01); *A61B 8/5223* (2013.01)

(58) Field of Classification Search
CPC .............................. A61B 8/4444; A61B 8/429
USPC ............................................. 600/438; 601/2
See application file for complete search history.

(56) References Cited

U.S. PATENT DOCUMENTS

| 6,511,427 B1* | 1/2003 | Sliwa, Jr. | A61B 5/4869 600/438 |
| 2004/0236223 A1* | 11/2004 | Barnes | A61B 5/0048 600/459 |
| 2007/0232916 A1* | 10/2007 | Waki | A61B 5/6843 600/444 |
| 2009/0148012 A1* | 6/2009 | Altmann | A61B 6/5247 382/128 |
| 2009/0274357 A1* | 11/2009 | Wilson | G01N 33/12 382/131 |
| 2010/0036243 A1* | 2/2010 | Matsumura | A61B 8/08 600/438 |
| 2011/0166453 A1 | 7/2011 | Anthony et al. | |

(Continued)

OTHER PUBLICATIONS

Kerins, Brandon, "Skin Harness and Elasticity Measurement Device", ME 450 Fall 2010.*

*Primary Examiner* — Tse Chen
*Assistant Examiner* — Joanne Hoffman
(74) *Attorney, Agent, or Firm* — McDermott Will & Emery LLP

(57) ABSTRACT

Provided are an ultrasound system and a method of detecting a pressure applied to an object through an ultrasound probe. The ultrasound system includes: an ultrasound data acquiring unit configured to acquire, by using an ultrasound probe including a strain gauge that is strained by a pressure applied thereto and has a damping factor and an elasticity factor, ultrasound data corresponding to an object; and a processor configured to generate an ultrasound image by using the ultrasound data, calculate a strain rate of the strain gauge caused by the pressure by using the ultrasound image, and detect the pressure by using the strain rate calculated.

36 Claims, 12 Drawing Sheets

(56) References Cited

U.S. PATENT DOCUMENTS

2011/0251636 A1* 10/2011 McEwen ................ A61B 5/489
  606/202
2012/0165669 A1  6/2012 Barley et al.

* cited by examiner

ULTRASOUND SYSTEM AND METHOD OF DETECTING PRESSURE APPLIED TO OBJECT

RELATED APPLICATIONS

This application claims the benefit of Korean Patent Application No. 10-2013-0061038, filed on May 29, 2013, in the Korean Intellectual Property Office, the disclosure of which is incorporated herein in its entirety by reference.

BACKGROUND

1. Field

One or more embodiments of the present invention relate to ultrasound systems, and more particularly, to ultrasound systems and methods of detecting a pressure applied to an object through an ultrasound probe.

2. Description of the Related Art

Since ultrasound systems have noninvasive and nondestructive characteristics, they are widely used medical treatment for obtaining information from an object. Such ultrasound systems are very important in the field of medical treatment because they may provide medical practitioners with real-time high-resolution images of internal organs of an object without performing a surgical operation by directly incising and observing inner parts of the object.

An ultrasound system uses an ultrasound probe to transmit an ultrasound signal to an object and to receive an ultrasound signal (i.e., an ultrasound echo signal) reflected from the object. Also, the ultrasound system generates an ultrasound image corresponding to the object by using a received ultrasound echo signal.

In general, the ultrasound probe transmits an ultrasound signal to the object while contacting a surface of the object and receives an ultrasound echo signal reflected from the object. Therefore, since a force (i.e., pressure) applied by a user is applied to the object through the ultrasound probe, strain may occur in the object, and thus, the ultrasound image may be distorted.

SUMMARY

One or more embodiments of the present invention include ultrasound systems and methods of detecting a pressure applied to an object through an ultrasound probe, by using a material (hereinafter referred to as a strain gauge) that is provided at one side of the ultrasound probe and has a predetermined thickness, a predetermined damping value, and a predetermined elasticity value, or by using a strain gauge and a pressure sensor.

Additional aspects will be set forth in part in the description which follows and, in part, will be apparent from the description, or may be learned by practice of the presented embodiments.

According to one or more embodiments of the present invention, an ultrasound system includes: an ultrasound data acquiring unit configured to acquire, by using an ultrasound probe including a strain gauge that is strained by a pressure applied thereto and has a damping factor and an elasticity factor, ultrasound data corresponding to an object; and a processor configured to generate an ultrasound image by using the ultrasound data, calculate a strain rate of the strain gauge caused by the pressure applied thereto by using the ultrasound image, and detect the pressure by using the calculated strain rate.

According to one or more embodiments of the present invention, a method of detecting a pressure includes: acquiring, by using an ultrasound probe including a strain gauge that is strained by a pressure applied thereto and has a damping factor and an elasticity factor, ultrasound data corresponding to an object; generating an ultrasound image by using the ultrasound data; calculating a strain rate of the strain gauge caused by the pressure applied thereto by using the ultrasound image; and detecting the pressure applied to the strain gauge by using the calculated strain rate.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
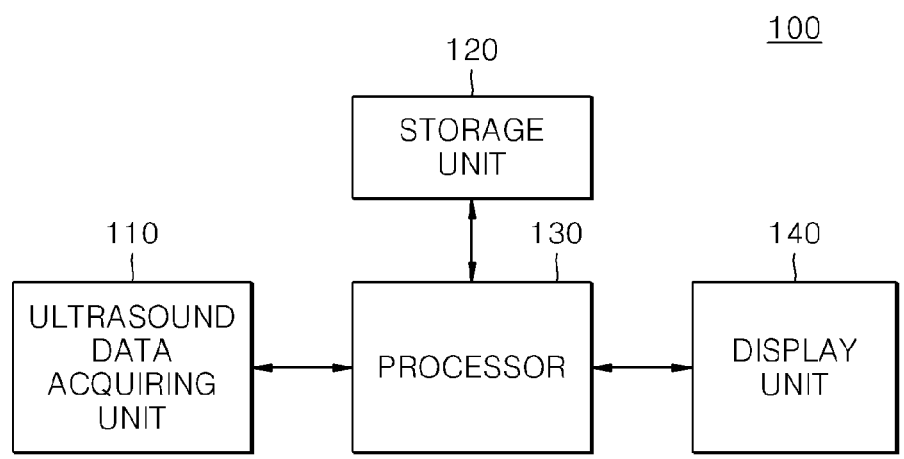
FIG. 1 is a block diagram illustrating a configuration of an ultrasound system according to an embodiment of the present invention.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Hereinafter, embodiments of the present invention will be described in detail with reference to the accompanying drawings.

FIG. 1 is a block diagram illustrating a configuration of an ultrasound system according to an embodiment of the present invention. Referring to FIG. 1, an ultrasound system 100 includes an ultrasound data acquiring unit 110, a storage unit 120, a processor 130, and a display unit 140.

The ultrasound data acquiring unit 110 acquires ultrasound data corresponding to an ultrasound image of an object. The object includes a target (for example, a liver, a heart, a bone, or a blood vessel). The ultrasound data includes radio frequency (RF) data. However, the ultrasound data is not limited thereto.

Figure 2:
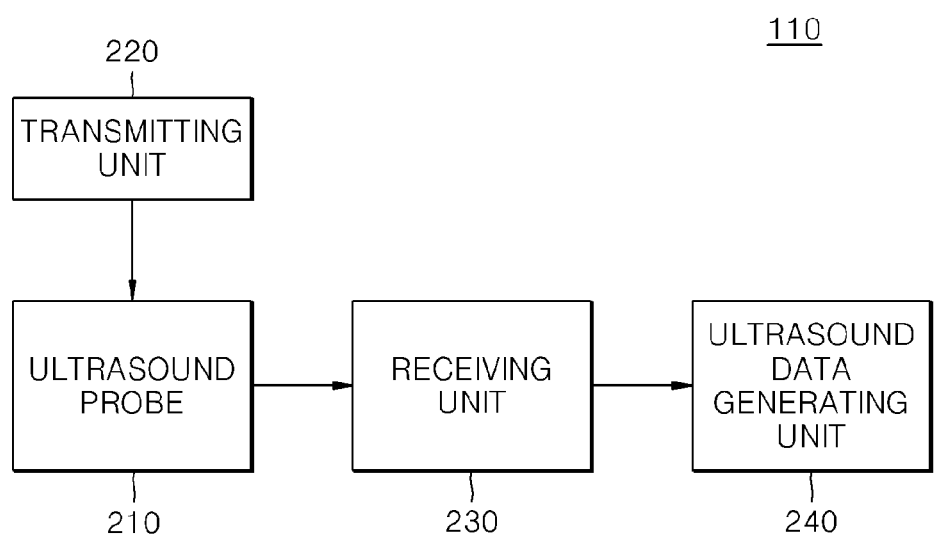
FIG. 2 is a block diagram illustrating a configuration of an ultrasound data acquiring unit according to an embodiment of the present invention.

FIG. 2 is a block diagram illustrating a configuration of the ultrasound data acquiring unit 110 according to an embodiment of the present invention. Referring to FIG. 2, the ultrasound data acquiring unit 110 includes an ultrasound probe 210, a transmitting unit 220, a receiving unit 230, and an ultrasound data generating unit 240.

The ultrasound probe 210 includes a plurality of transducer elements (not illustrated) that convert an electrical/ultrasound signal into an ultrasound/electrical signal. The ultrasound probe 210 transmits an ultrasound signal to the object and receives an ultrasound signal (i.e., an ultrasound echo signal) reflected from the object to thereby generate an electrical signal (hereinafter referred to as a reception signal). The received signal includes an analog signal. For example, the ultrasound probe 210 includes a convex probe, a linear probe, a phased array probe, a three-dimensional (3D) probe, and a two-dimensional (2D) array probe.

In an embodiment, the ultrasound probe 210 includes an element, such as a strain gauge, which has a predetermined thickness, low-attenuation acoustic characteristics, a predetermined damping value, and a predetermined elasticity value. In the description below, it is assumed that the element is a strain gauge. The strain gauge is attached to one side of the ultrasound probe 210 and strained by a pressure applied thereto through the ultrasound probe 210. The strain gauge includes a solid gel, silicon, and a fluid pocket. Hereinafter, for the convenience of description, the ultrasound probe 210 is considered to be a one-dimensional (1D) array probe or a 2D array probe, and the same reference numeral "210" will be used in both cases.

Figure 3:
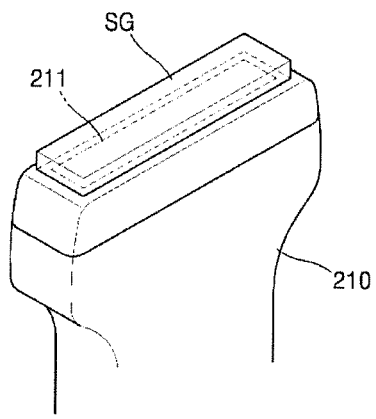
FIG. 3 is a diagram illustrating an example of a strain gauge attached to a one-dimensional (1D) array probe, according to an embodiment of the present invention.

FIG. 3 is a diagram illustrating an example of a strain gauge SG attached to a 1D array probe 210, according to an embodiment of the present invention. As illustrated in FIG. 3, the strain gauge SG is attached onto a lens 211 of the 1D array probe 210 (for example, a linear probe, a phased array probe, a convex probe, or a 3D probe) and contacts a surface of an object.

Figure 4:
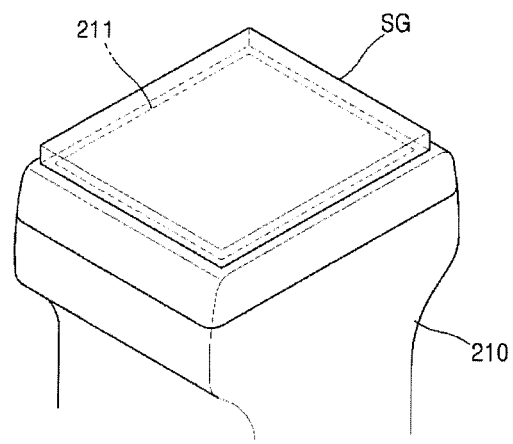
FIG. 4 is a diagram illustrating an example of a strain gauge attached to a two-dimensional (2D) array probe, according to an embodiment of the present invention.

FIG. 4 is a diagram illustrating an example of a strain gauge SG attached to a 2D array probe 210, according to an embodiment of the present invention. As illustrated in FIG. 4, the strain gauge SG is attached onto a lens 211 of the 2D array probe 210 and contacts a surface of the object.

In another embodiment, the ultrasound probe 210 includes a strain gauge and a pressure sensor. As in the above embodiment, the strain gauge is attached to one side of the ultrasound probe 210 and strained by a pressure applied thereto through the ultrasound probe 210, and includes a solid gel, silicon, and a fluid pocket. The pressure sensor is attached to one side of the ultrasound probe 210 to measure a pressure applied thereto through the ultrasound probe 210 to thereby output pressure measurement information. The pressure sensor may be any device that measures the pressure applied thereto through the ultrasound probe 210.

Figure 5:
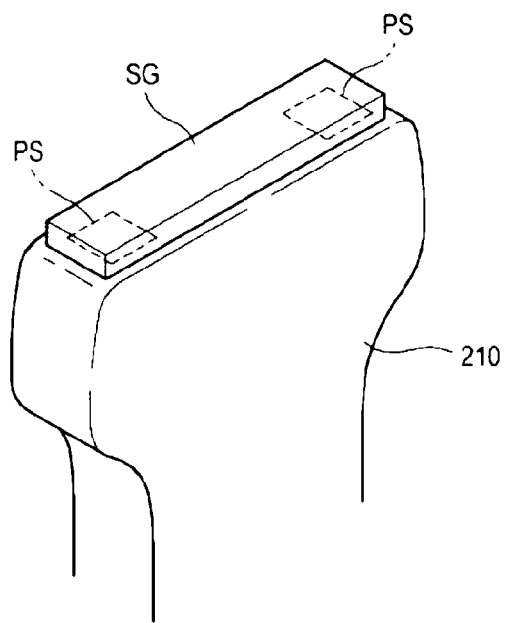
FIG. 5 is a diagram illustrating an example of a strain gauge and a pressure sensor attached to a 1D array probe, according to another embodiment of the present invention.

FIG. 5 is a diagram illustrating an example of a strain gauge SG and a pressure sensor attached to a 1D array probe 210, according to another embodiment of the present invention. As illustrated in FIG. 5, a strain gauge SG is attached onto a lens 211 of the 1D array probe 210 and contacts a surface of an object. Also, a pressure sensor PS is attached to a surface identical to a surface of the lens 211 of the 1D array probe 210, or inside the lens 211 to measure a pressure applied to the object through the 1D array probe 210 to thereby generate measurement information.

In the above embodiment, it has been described that two pressure sensors are attached to the 1D array probe 210. However, embodiments of the present invention are not limited thereto, and a plurality of pressure sensors may be attached to the 1D array probe 210.

Figure 6:
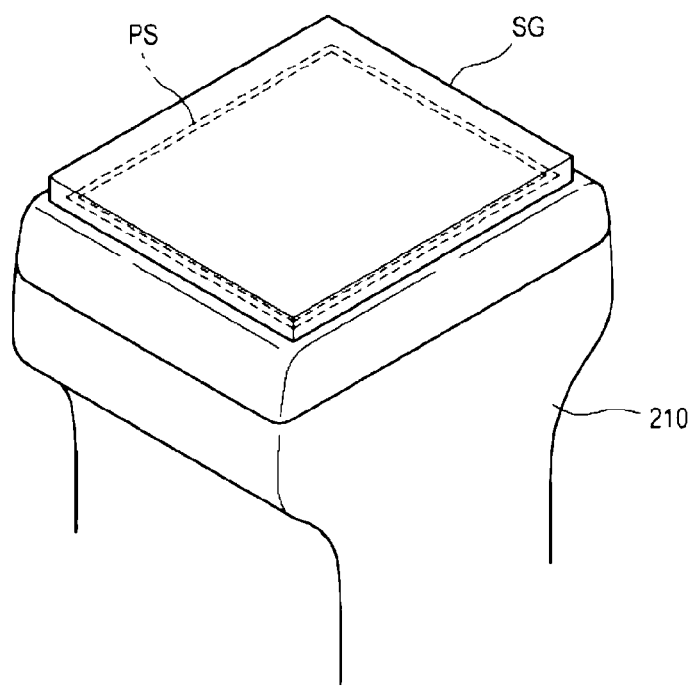
FIG. 6 is a diagram illustrating an example of a strain gauge and a pressure sensor attached to a 2D array probe, according to another embodiment of the present invention.

FIG. 6 is a diagram illustrating an example of a strain gauge SG and a pressure sensor attached to a 2D array probe 210, according to another embodiment of the present invention. As illustrated in FIG. 6, as in the above embodiment, the strain gauge SG is attached onto a lens 211 of the 2D array probe 210 and contacts a surface of the object. Also, a pressure sensor PS in a predetermined configuration (for example, a rectangular ring configuration) is attached to a surface identical to a surface of the lens 211 of the 2D array probe 210, or inside the lens 211 to measure a pressure applied to the object through the 2D array probe 210, to generate measurement information.

Referring to FIG. 2, the transmitting unit 220 controls transmission of the ultrasound signal. Also, in consideration of a transducer element and a focus point, the transmitting unit 220 generates an electrical signal (hereinafter referred to a transmission signal) that is used to obtain the ultrasound image. Therefore, the ultrasound probe 210 converts the transmission signal, received from the transmitting unit 220, into an ultrasound signal, transmits the ultrasound signal to the object, and receives the ultrasound echo signal reflected from the object to thereby generate the reception signal.

The receiving unit 230 converts the reception signal received from the ultrasound probe 210 into a digital signal. Also, in consideration of the transducer element and the focus point, the receiving unit 230 performs reception beamforming on the digital signal to generate a reception focus signal. Since the reception beamforming may be performed by various well-known methods, a detailed description thereof will be omitted herein.

The ultrasound data generating unit 240 generates, by using the reception focus signal received from the receiving unit 230, ultrasound data corresponding to the ultrasound image. Also, the ultrasound data generating unit 240 may perform various signal processing (for example, gain control) on the reception focus signal to generate the ultrasound data.

Referring to FIG. 1, the storage unit 120 stores the ultrasound data obtained by the ultrasound data acquiring unit 110. Also, the storage unit 120 stores the length, damping value (damping factor), and elasticity value (elasticity factor) of the strain gauge SG attached to the ultrasound probe 210. The length of the strain gauge SG refers to the length in a direction perpendicular to the length direction of the transducer element of the ultrasound probe 210, that is, the length in a direction (axis direction) in which the ultrasound signal is transmitted and received. Also, the storage unit 120 stores a pressure-dependent strain rate of each target of the object.

The processor 130 is connected to the ultrasound data acquiring unit 110 and the storage unit 120. For example, the processor 130 includes a central processing unit (CPU), a microprocessor, and a graphic processing unit (GPU).

Figure 7:
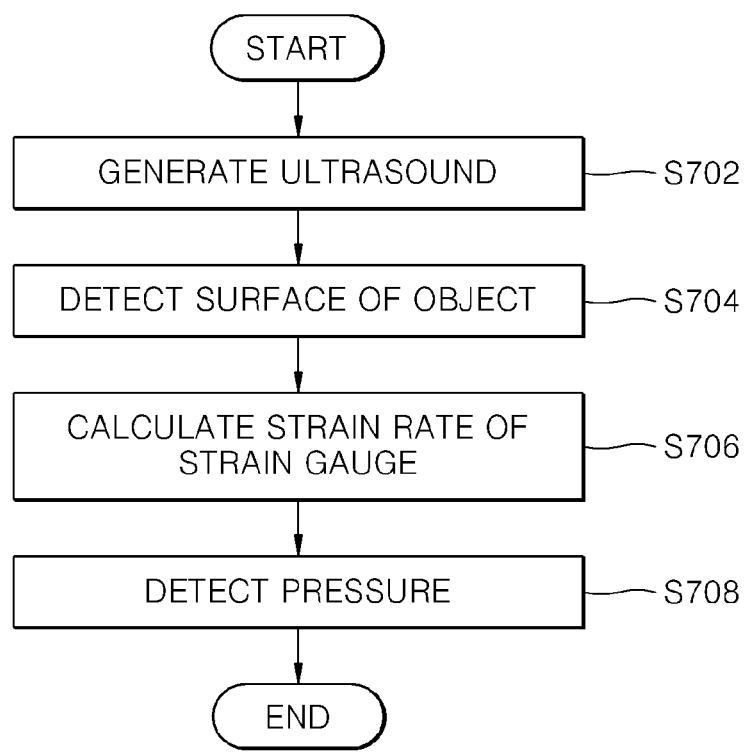
FIG. 7 is a flowchart illustrating a process of detecting a pressure applied to an object, according to an embodiment of the present invention.

FIG. 7 is a flowchart illustrating a process of detecting a pressure applied to an object, according to an embodiment of the present invention. Referring to FIG. 7, the processor 130 generates an ultrasound image by using the ultrasound data received from the ultrasound data acquiring unit 110 (S702). The ultrasound image includes a 2D ultrasound image or a 3D ultrasound image.

The processor 130 performs edge detection on the ultrasound image to detect a surface of the object (S704). The edge may be detected by using an edge mask, such as, a Sobel mask, a Prewitt mask, a Robert mask, or a Canny mask. Alternatively, the edge may be detected from an eigenvalue difference by using a structure tensor. In the present embodiment, the processor 130 may detect the surface of the object by performing edge detection in the axis direction with respect to a pixel (or voxel) corresponding to the first row, from among the pixels (or voxels) of the ultrasound image.

Based on the detected surface of the object, the processor 130 calculates a strain rate representing a degree to which the strain gauge SG is strained by the pressure applied through the ultrasound probe 210 (S706).

Figure 8:
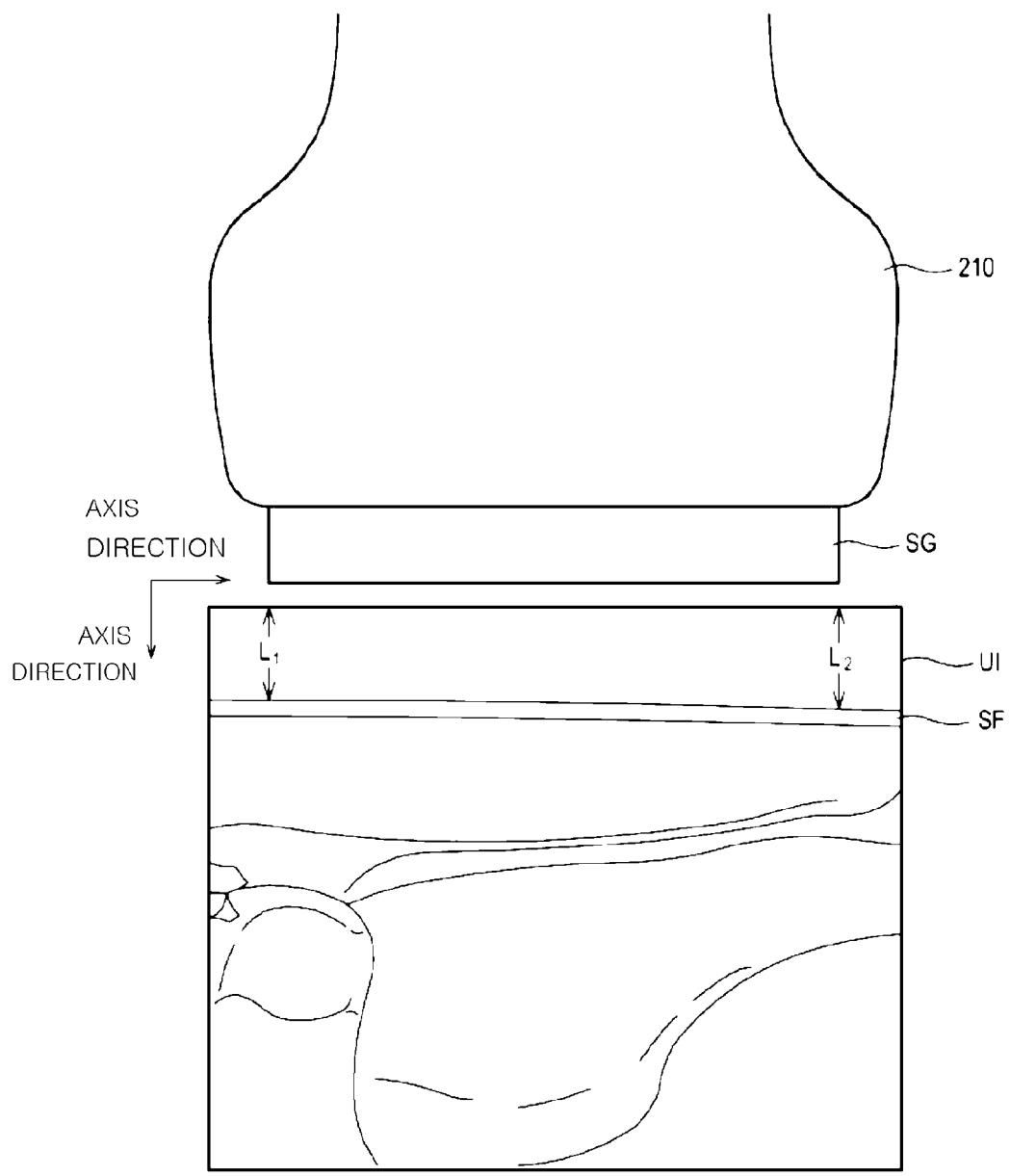
FIGS. 8 and 9 are diagrams illustrating an example in which a uniform pressure is applied through the 1D array probe to an object, according to an embodiment of the present invention.
Figure 9:
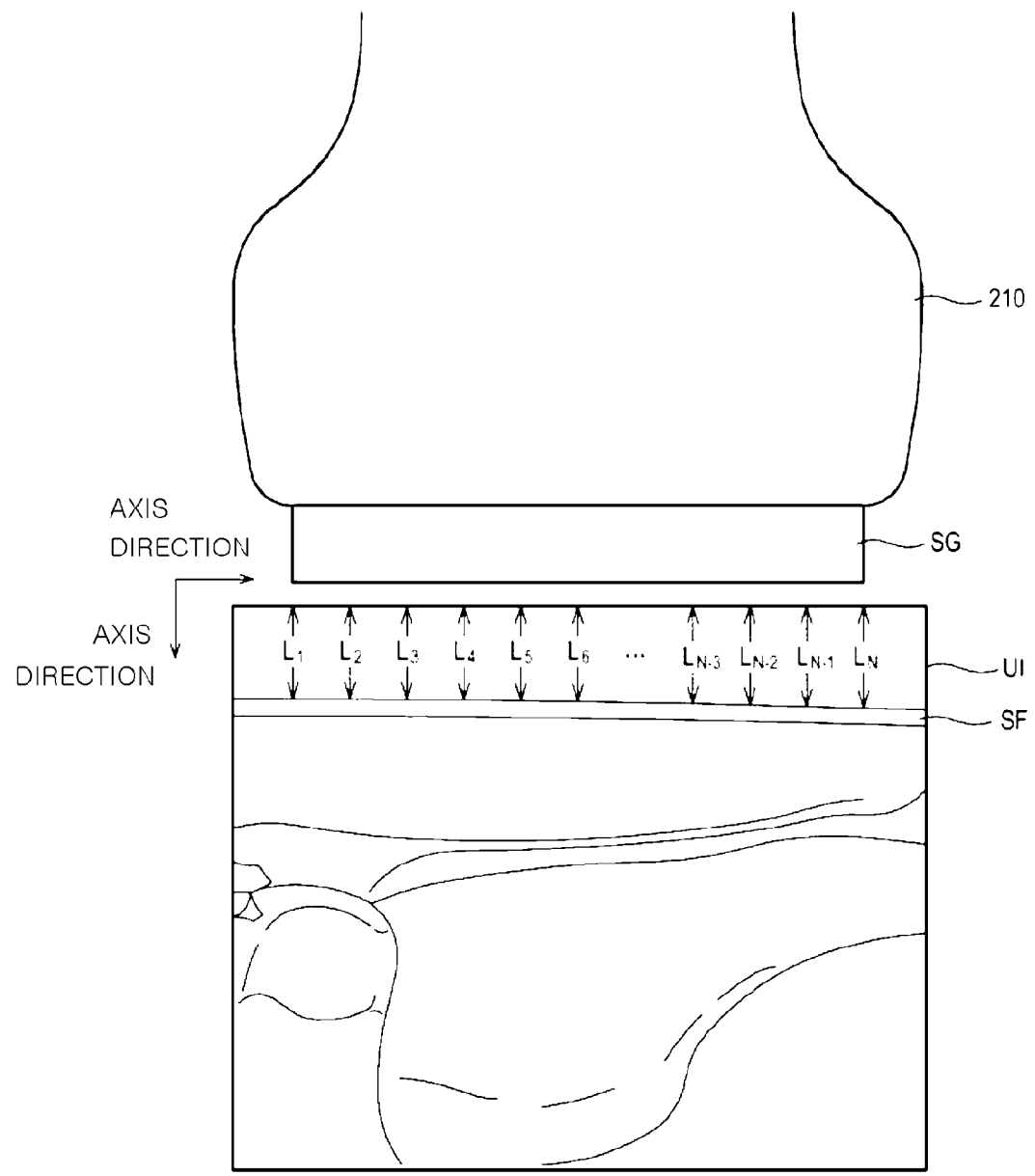

FIGS. 8 and 9 are diagrams illustrating an example in which a uniform pressure is applied through the ultrasound probe (1D array probe), according to an embodiment of the present invention. Referring to FIG. 8, the processor 130 calculates strain rates $L_1$ and $L_2$ at both ends of the ultrasound probe (1D array probe) 210 with respect to a surface SF of the object that is detected from an ultrasound image (2D ultrasound image) UI. Since the strain rates may be calculated by various well-known methods, a detailed description thereof will be omitted herein. Referring to FIG. 9, the processor 130 calculates a strain rate $L_i$ ($1 \leq i \leq N$) at predetermined intervals with respect to a surface SF of the object that is detected from an ultrasound image (2D ultrasound image) UI.

Figure 10:
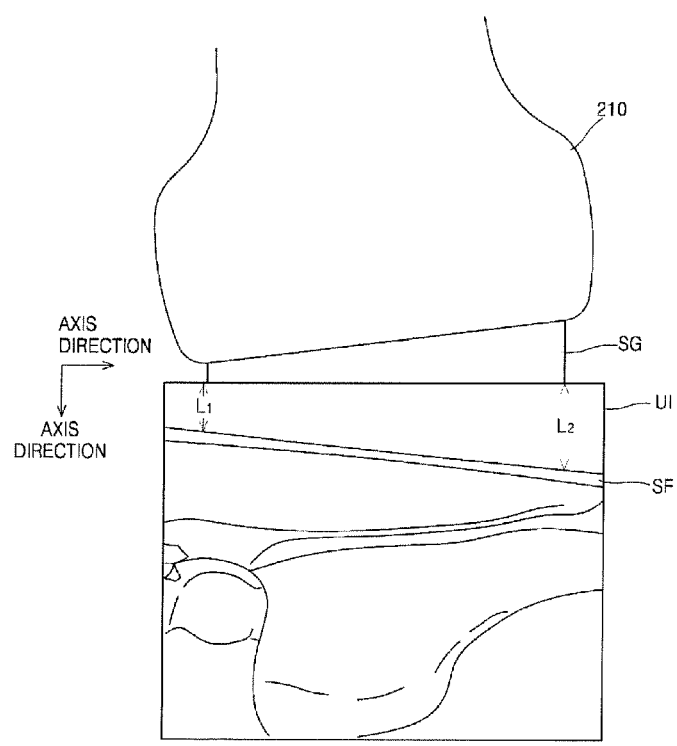
FIGS. 10 and 11 are diagrams illustrating an example in which a non-uniform pressure is applied through the 1D array probe to an object, according to an embodiment of the present invention.
Figure 11:
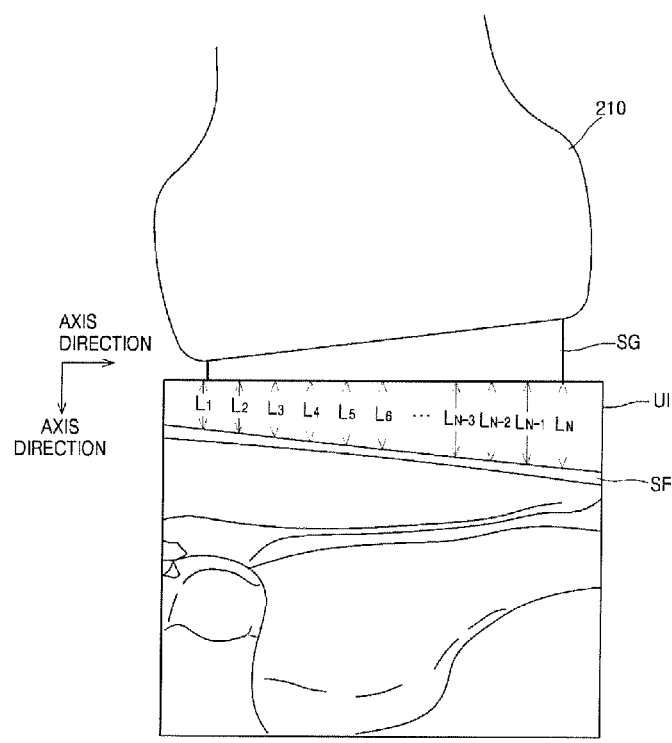

FIGS. 10 and 11 are diagrams illustrating an example in which a non-uniform pressure is applied through the ultrasound probe (1D array probe), according to an embodiment of the present invention. Referring to FIG. 10, the processor 130 calculates strain rates $L_1$ and $L_2$ at both ends of the ultrasound probe (1D array probe) 210 with respect to a surface SF of the object that is detected from an ultrasound image (2D ultrasound image) UI. Referring to FIG. 11, the processor 130 calculates a strain rate $L_i$ ($1 \leq i \leq N$) at predetermined intervals in the lateral direction of an ultrasound image UI with respect to a surface SF of the object that is detected from the ultrasound image (2D ultrasound image) UI.

Figure 12:
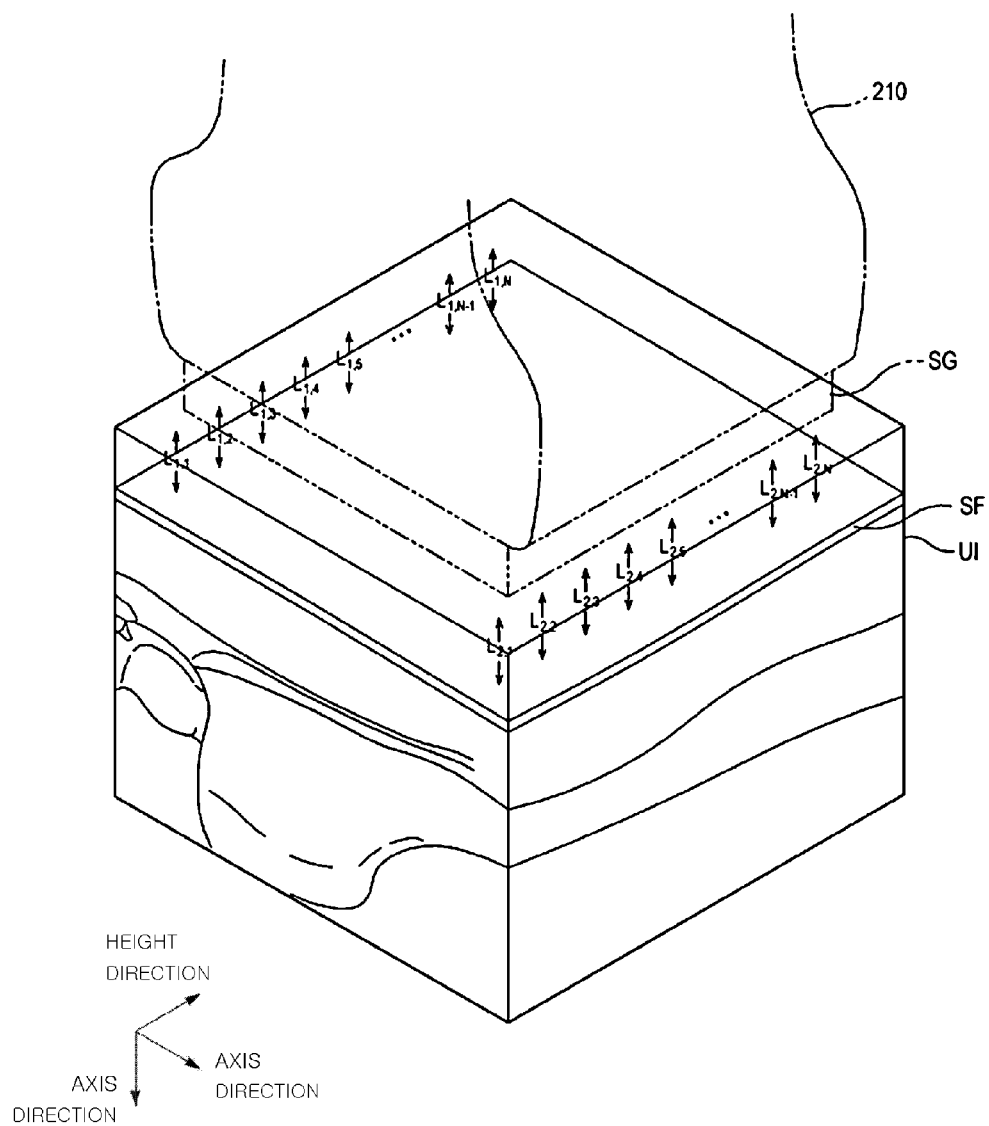
FIGS. 12 and 13 are diagrams illustrating an example in which a uniform pressure is applied through the 2D array probe to an object, according to another embodiment of the present invention.
Figure 13:
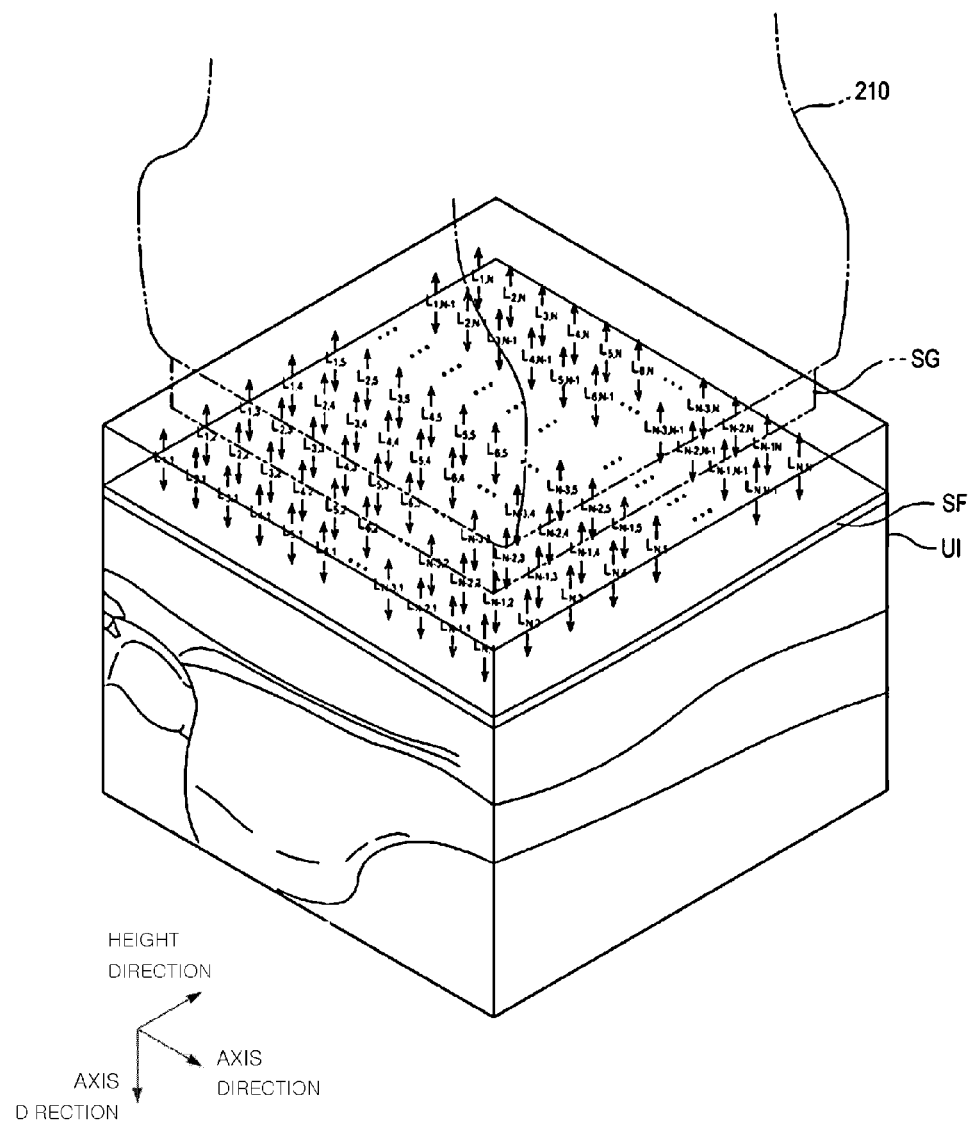

FIGS. 12 and 13 are diagrams illustrating an example in which a uniform pressure is applied through the ultrasound probe (2D array probe), according to another embodiment of the present invention. Referring to FIG. 12, the processor 130 calculates strain rates $L_{1,1}$, $L_{1,2}$, ..., $L_{1,N}$, $L_{2,1}$, $L_{2,2}$, ..., $L_{2,N}$ at both ends of the ultrasound probe (2D array probe) 210 at predetermined intervals in the height direction of an ultrasound image UI with respect to a surface SF of the object that is detected from the ultrasound image (3D ultrasound image) UI. Referring to FIG. 13, the processor 130 calculates a strain rate $L_1$ ($1 \leq l,j \leq N$) at predetermined intervals in the lateral direction and the height direction of an ultrasound image UI with respect to a surface SF of the object that is detected from the ultrasound image (3D ultrasound image) UI.

Figure 14:
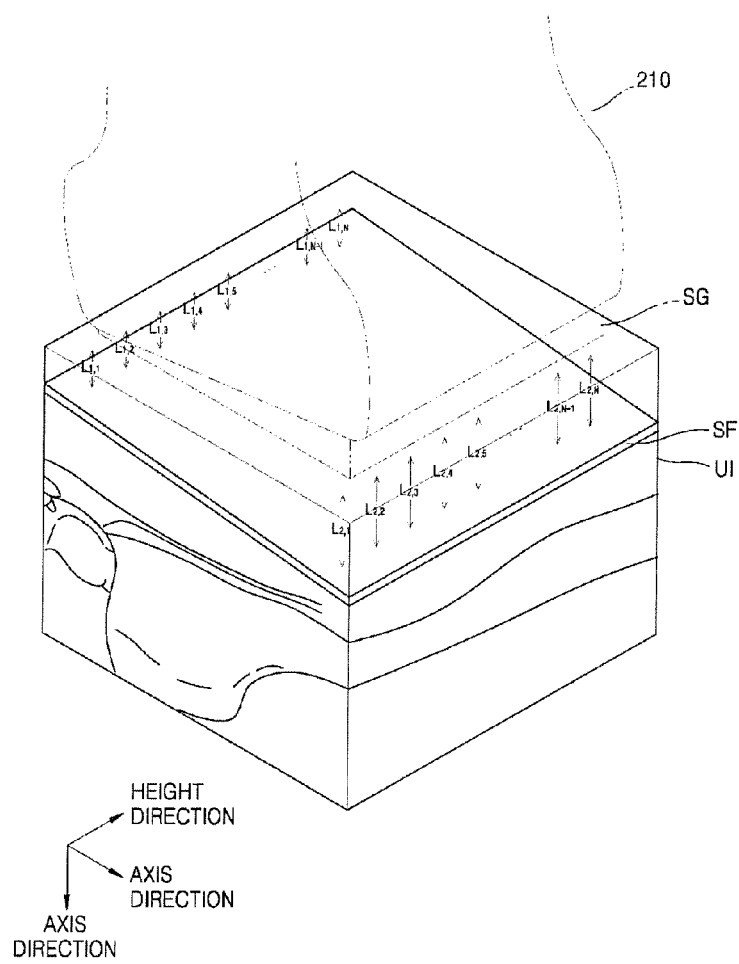
FIGS. 14 and 15 are diagrams illustrating an example in which a non-uniform pressure is applied through the 2D array probe to an object, according to another embodiment of the present invention.
Figure 15:
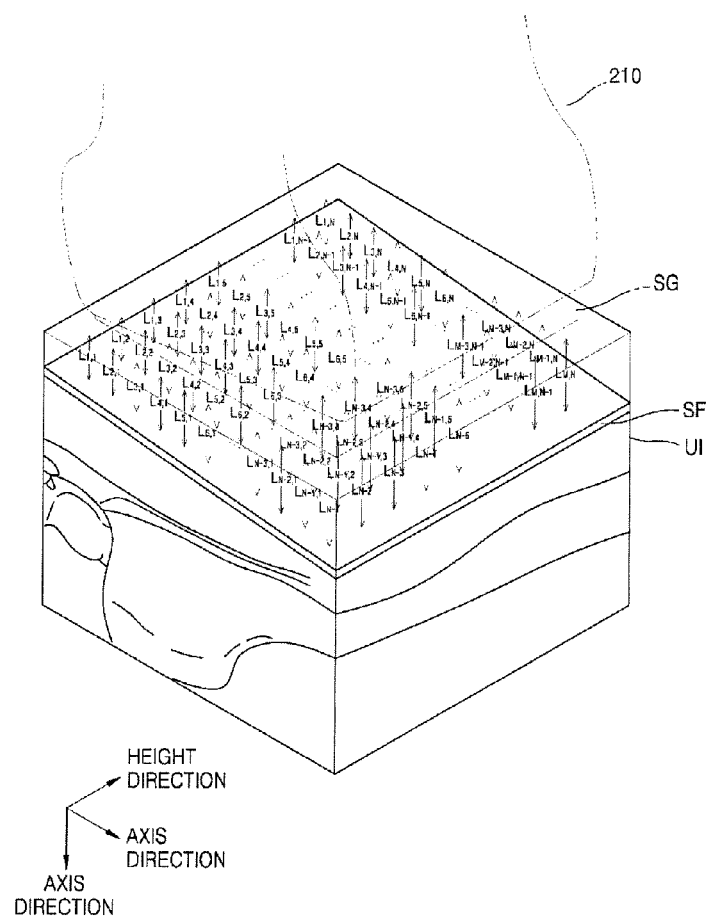

FIGS. 14 and 15 are diagrams illustrating an example in which a non-uniform pressure is applied through the ultrasound probe (2D array probe), according to another embodiment of the present invention. Referring to FIG. 14, the processor 130 calculates strain rates $L_{1,1}$, $L_{1,2}$, ..., $L_{1,N}$, $L_{2,1}$, $L_{2,2}$, ..., $L_{2,N}$ at both ends of the ultrasound probe (2D array probe) 210 in the height direction of an ultrasound image UI with respect to a surface SF of the object that is detected from the ultrasound image (3D ultrasound image) UI. Referring to FIG. 15, the processor 130 calculates a strain rate $L_{i,j}$ ($1 \leq l,j \leq N$) at predetermined intervals in the lateral direction and the height direction of an ultrasound image UI with respect to a surface SF of the object that is detected from the ultrasound image (3D ultrasound image) UI.

Referring to FIG. 7, the processor 130 detects a pressure applied to the object through the ultrasound probe 210 (S708). In an embodiment, the processor 120 detects the pressure applied to the object based on the strain rate of the strain gauge SG.

As an example, the processor 130 calculates the pressure F corresponding to each of the strain rates $L_1$ and $L_2$ of the strain gauge SG by applying the calculated strain rates $L_1$ and $L_2$ of the strain gauge SG, the damping factor (damping value), and the elasticity factor (elasticity value), which are stored in the storage unit 120, to Equation 1 as illustrated in FIGS. 8 and 10.

$$F = mx'' + cx' + kx \qquad \text{[Equation 1]}$$

In Equation 1, m denotes the mass of the strain gauge SG, c denotes the damping factor (damping value) of the strain gauge SG, k denotes the elasticity factor (elasticity value) of the strain gauge SG, x denotes the length of the strain gauge SG, x' denotes a velocity term obtained by temporally differentiating the length x, and x'' denotes an acceleration term obtained by temporally differentiating the length x twice, which is discarded in the present embodiment.

Alternatively, the processor 130 may estimate the pressure applied to the object at predetermined intervals, as illustrated in FIGS. 9 and 11, by interpolating the pressure F corresponding to each of the calculated strain rates $L_1$ and $L_2$ of the strain gauge SG with respect to the surface SF of the object.

As another example, the processor 130 calculates the pressure F corresponding to each of the strain rates $L_i$ ($1 \leq i \leq N$) of the strain gauge SG by applying the calculated strain rates $L_i$ ($1 \leq i \leq N$) of the strain gauge SG to Equation 1 as illustrated in FIGS. 9 and 11.

As another example, the processor 130 calculates the pressure F corresponding to each of the strain rates strain rates $L_{1,1}$, $L_{1,2}$, ..., $L_{1,N}$, $L_{2,1}$, $L_{2,2}$, ..., $L_{2,N}$ of the strain gauge SG by applying the calculated strain rates $L_{1,1}$, $L_{1,2}$, ..., $L_{1,N}$, $L_{2,1}$, $L_{2,2}$, ..., $L_{2,N}$ of the strain gauge SG to Equation 1 as illustrated in FIGS. 12 and 14.

Alternatively, the processor 130 may estimate the pressure applied to the object at predetermined intervals, as illustrated in FIGS. 13 and 15, by interpolating the pressure F corresponding to each of the calculated strain rates $L_{1,1}$, $L_{1,2}$, ..., $L_{1,N}$, $L_{2,1}$, $L_{2,2}$, ..., $L_{2,N}$ of the strain gauge SG with respect to the surface SF of the object.

As another example, the processor 130 calculates the pressure F corresponding to each of the strain rates $L_{i,j}$ ($1 \leq i,j \leq N$) of the strain gauge SG by applying the calculated strain rates $L_{i,j}$ ($1 \leq i,j \leq N$) of the strain gauge SG to Equation 1, as illustrated in FIGS. 13 and 15.

In another embodiment, the processor 130 calculates, based on the calculated strain rate of the strain gauge SG, a pressure (hereinafter referred to as a first pressure) corresponding to the strain rate of the strain gauge SG. The processor 130 calculates, based on the measurement information received from the pressure sensor PS, a pressure (hereinafter referred to as a second pressure) corresponding to the measurement information. Then, based on the first pressure and the second pressure, the processor 130 detects the pressure applied to the object through the ultrasound probe 210. For example, the processor 130 detects an average value of the first pressure and the second pressure as the pressure applied to the object.

In the above embodiment, it has been described that the average value of the first pressure and the second pressure is detected as the pressure applied to the object; however, embodiments of the present invention are not limited thereto.

Alternatively, the processor 130 generates pressure information including the detected pressure F, and controls a display of the pressure information. The pressure information may be displayed in various shapes (for example, as a text, a numerical value, or a graph)

Alternatively, the processor 130 may perform image compensation processing on the ultrasound image UI by using the detected pressure F. Since the image compensation processing may be performed by various well-known methods, a detailed description thereof will be omitted herein.

Alternatively, the processor 130 may perform image compensation processing on the ultrasound image UI by using the detected pressure F and the strain rate of each target stored in the storage unit 120.

Referring to FIG. 1, the display unit 140 displays the ultrasound image generated by the processor 130. Also, the display unit 140 displays the pressure information generated by the processor 130.

As described above, according to the one or more of the above embodiments of the present invention, the pressure applied to an object through the ultrasound probe may be accurately detected by using the strain gauge or by using the strain gauge and the pressure sensor.

Also, the ultrasound image may be compensated by using the detected pressure.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:
1. An ultrasound system comprising:
an ultrasound probe;
a strain gauge having a damping factor and an elasticity factor, strained by a pressure applied thereto, and directly attached onto a surface of a lens of the ultrasound probe;
an ultrasound data acquiring unit configured to acquire ultrasound data corresponding to an object through the ultrasound probe;
a storage configured to store data related to the pressure applied to the strain gauge, strain rates representing a degree to which the strain gauge is strained by the pressure applied thereto, the damping factor of the strain gauge, and the elasticity factor of the strain gauge; and
a processor configured to generate an ultrasound image by using the ultrasound data, detect a surface of the object based on the ultrasound image, calculate the strain rates between opposite ends of the ultrasound probe based on a degree to which the strain gauge is strained upon the detected surface of the object, detect the pressure corresponding to each of the strain rates of the strain gauge by using the calculated strain rates and the stored data, and perform image compensation processing on the ultrasound image based on the detected pressure.

2. The ultrasound system of claim 1, wherein the strain gauge comprises a solid gel, silicon, or a liquid pocket.

3. The ultrasound system of claim 1, wherein the processor is configured to detect the surface of the object by performing edge detection on the ultrasound image.

4. The ultrasound system of claim 1, wherein the ultrasound probe comprises a one-dimensional (1D) array probe.

5. The ultrasound system of claim 1, wherein the processor is configured to calculate the pressure by using the strain rates, the damping factor, and the elasticity factor.

6. The ultrasound system of claim 5, wherein the processor is configured to calculate the pressure in the ultrasound image at predetermined intervals in a lateral direction of the ultrasound image by performing compensation processing on the calculated pressure.

7. The ultrasound system of claim 4, wherein the processor is configured to calculate the strain rates in the ultrasound image at predetermined intervals in a lateral direction of the ultrasound image based on the surface of the object.

8. The ultrasound system of claim 7, wherein the processor is configured to calculate the pressure by using the strain rates, the damping factor, and the elasticity factor.

9. The ultrasound system of claim 1, wherein the ultrasound probe comprises a two-dimensional (2D) array probe.

10. The ultrasound system of claim 9, wherein the processor is configured to calculate the strain rates between the opposite ends of the ultrasound probe at predetermined intervals in a lateral direction of the ultrasound image based on the surface of the object.

11. The ultrasound system of claim 10, wherein the processor is configured to calculate the pressure by using the strain rates, the damping factor, and the elasticity factor.

12. The ultrasound system of claim 9, wherein the processor is configured to calculate the strain rates in the ultrasound image at predetermined intervals in the lateral direction and a height direction of the ultrasound image based on the surface of the object.

13. The ultrasound system of claim 12, wherein the processor is configured to calculate the pressure by using the strain rates, the damping factor, and the elasticity factor.

14. The ultrasound system of claim 1, further comprising a pressure sensor attached to one side of the ultrasound probe and configured to measure a pressure applied to the object and generate measurement information.

15. The ultrasound system of claim 14, wherein the pressure sensor is attached to the surface of the lens of the ultrasound probe, or inside the lens.

16. The ultrasound system of claim 14, wherein the processor is configured to:
calculate a first pressure corresponding to the measurement information, based on the measurement information; and detect the pressure applied to the object, based on a second pressure corresponding to the strain rates and the first pressure corresponding to the measurement information.

17. The ultrasound system of claim 16, wherein the processor is configured to detect an average value of the second pressure corresponding to the strain rates and the first pressure corresponding to the measurement information as the pressure applied to the object.

18. The ultrasound system of claim 1, wherein the processor is further configured to:
generate pressure information comprising the detected pressure; and
control a display of the pressure information.

19. A method of detecting a pressure, comprising:
storing data related to a pressure applied, through an ultrasound probe, to a strain gauge directly attached onto a surface of a lens of the ultrasound probe, strain rates representing a degree to which the strain gauge is strained by the pressure applied thereto, a damping factor of the strain gauge, and an elasticity factor of the strain gauge;
acquiring, by using the ultrasound probe comprising the strain gauge, ultrasound data corresponding to an object when the pressure is being applied;
generating an ultrasound image by using the ultrasound data;
detecting a surface of the object based on the ultrasound image;
calculating the strain rates between opposite ends of the ultrasound probe based on a degree to which the strain gauge is strained upon the detected surface of the object;
detecting the pressure corresponding to each of the strain rates of the strain gauge by using the calculated strain rates and the stored data; and
performing image compensation processing on the ultrasound image based on the detected pressure.

20. The method of claim 19, wherein the strain gauge comprises a solid gel, silicon, or a liquid pocket.

21. The method of claim 19, wherein the detecting the surface of the object based on the ultrasound image comprises detecting the surface of the object by performing edge detection on the ultrasound image.

22. The method of claim 19, wherein the ultrasound probe comprises a one-dimensional (1D) array probe.

23. The method of claim 19, wherein the detecting of the pressure comprises calculating the pressure by using the strain rates, the damping factor, and the elasticity factor.

24. The method of claim 23, wherein the detecting of the pressure comprises calculating the pressure in the ultrasound image at predetermined intervals in a lateral direction of the ultrasound image by performing compensation processing on the calculated pressure.

25. The method of claim 22, wherein calculating the strain rates based on a degree to which the strain gauge is strained upon the detected surface of the object comprises calculating the strain rates in the ultrasound image at predetermined intervals in a lateral direction of the ultrasound image based on the surface of the object.

26. The method of claim 25, wherein the detecting of the pressure comprises calculating the pressure by using the strain rates, the damping factor, and the elasticity factor.

27. The method of claim 19, wherein the ultrasound probe comprises a two-dimensional (2D) array probe.

28. The method of claim 27, wherein calculating the strain rates based on a degree to which the strain gauge is strained upon the detected surface of the object comprises calculating the strain rates between the opposite ends of the ultrasound probe at predetermined intervals in a lateral direction of the ultrasound image based on the surface of the object.

29. The method of claim 28, wherein the detecting of the pressure comprises calculating the pressure by using the strain rates, the damping factor, and the elasticity factor.

30. The method of claim 27, wherein calculating the strain rates based on a degree to which the strain gauge is strained upon the detected surface of the object comprises calculating the strain rates in the ultrasound image at predetermined intervals in a lateral direction and a height direction of the ultrasound image based on the surface of the object.

31. The method of claim 30, wherein the detecting of the pressure comprises calculating the pressure by using the strain rates, the damping factor, and the elasticity factor.

32. The method of claim 19, further comprising measuring a pressure applied to the object and generating measurement information, by using a pressure sensor attached to one side of the ultrasound probe.

33. The method of claim 32, wherein the pressure sensor is attached to the surface of the lens of the ultrasound probe, or inside the lens.

34. The method of claim 32, further comprising:
calculating, based on the measurement information, a first pressure corresponding to the measurement information; and
detecting the pressure applied to the object based on a second pressure corresponding to the strain rates and the first pressure corresponding to the measurement information.

35. The method of claim 34, wherein the detecting of the pressure applied to the object comprises detecting an average value of the second pressure corresponding to the strain rates and the first pressure corresponding to the measurement information as the pressure applied to the object.

36. The method of claim 19, further comprising:
generating pressure information comprising the detected pressure; and
controlling a display of the pressure information.

* * * * *